US012570944B2

(12) United States Patent
Stoianovici et al.

(10) Patent No.: US 12,570,944 B2
(45) Date of Patent: Mar. 10, 2026

(54) DEVICES AND METHODS FOR MAGNETIC ISOLATION AND ANALYSIS OF RARE CELLS

(71) Applicant: THE JOHNS HOPKINS UNIVERSITY, Baltimore, MD (US)

(72) Inventors: Dan Stoianovici, Reisterstown, MD (US); Kenneth J. Pienta, Glen Arm, MD (US); Michael A. Gorin, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 257 days.

(21) Appl. No.: 17/466,654

(22) Filed: Sep. 3, 2021

(65) Prior Publication Data

US 2021/0395666 A1 Dec. 23, 2021

Related U.S. Application Data

(63) Continuation of application No. 16/095,505, filed as application No. PCT/US2017/028746 on Apr. 21, 2017, now abandoned.

(Continued)

(51) Int. Cl.
*C12M 1/26* (2006.01)
*B01L 3/00* (2006.01)
(Continued)

(52) U.S. Cl.
CPC ............ *C12M 33/14* (2013.01); *B01L 3/502* (2013.01); *B01L 3/508* (2013.01); *B01L 3/5635* (2013.01);
(Continued)

(58) Field of Classification Search
CPC ..... G01N 33/54326; G01N 2001/4088; G01N 1/2813; G01N 1/312; G01N 1/4077; B01L 2200/0668; B01L 2300/0609
See application file for complete search history.

(56) References Cited

U.S. PATENT DOCUMENTS

| | | | |
|---|---|---|---|
| 8,728,411 B2 | 5/2014 | Beebe et al. | |
| 2007/0092876 A1 * | 4/2007 | Xu ..................... | C12N 15/1003 435/270 |
| 2014/0065622 A1 | 3/2014 | Beebe et al. | |

FOREIGN PATENT DOCUMENTS

| | | |
|---|---|---|
| RU | 2423698 C1 | 11/2009 |
| WO | 2004046305 A2 | 6/2004 |

OTHER PUBLICATIONS

Allard, W., et al., "Tumor Cells Circulate in the Peripheral Blood of All Major Carcinomas but not in Healthy Subjects or Patients With Nonmalignant Diseases", Clinical Cancer Research, vol. 10, 6897-6904, Oct. 15, 2004.

(Continued)

*Primary Examiner* — Gailene Gabel

(57) ABSTRACT

An embodiment in accordance with the present invention provides two devices for the isolation of rare cell populations such as circulating tumor cells (CTCs). Both devices use magnetic fields to manipulate cells that are bounded to paramagnetic particles (PMP). One device uses surface tension and a sieve for cell filtration, whereas the other allows for the direct transfer of cells onto a standard microscope slide. Subsequent processing steps may be directly performed on the devices thereby minimizing cell losses. The first device is referred to as the ST (surface tension) device and the second device is referred to as the DT (direct transfer) device. The ST device can also be considered as a chip for the isolation of the rare cell populations.

5 Claims, 5 Drawing Sheets

Related U.S. Application Data

(60) Provisional application No. 62/325,629, filed on Apr. 21, 2016.

(51) Int. Cl.

| | | |
|---|---|---|
| *C12M 1/00* | (2006.01) | |
| *C12M 1/12* | (2006.01) | |
| *C12M 3/06* | (2006.01) | |
| *G01N 1/28* | (2006.01) | |
| *G01N 1/31* | (2006.01) | |
| *G01N 1/40* | (2006.01) | |
| *G01N 33/543* | (2006.01) | |
| *G01N 35/00* | (2006.01) | |
| *G01N 15/10* | (2006.01) | |

(52) U.S. Cl.
CPC .............. *C12M 3/06* (2013.01); *C12M 25/02* (2013.01); *C12M 47/04* (2013.01); *G01N 1/2813* (2013.01); *G01N 1/312* (2013.01); *G01N 1/4077* (2013.01); *G01N 33/54326* (2013.01); *G01N 35/0098* (2013.01); *B01L 2200/025* (2013.01); *B01L 2200/026* (2013.01); *B01L 2200/0631* (2013.01); *B01L 2200/0668* (2013.01); *B01L 2300/0609* (2013.01); *B01L 2300/087* (2013.01); *B01L 2400/043* (2013.01); *G01N 2001/4088* (2013.01); *G01N 2015/1006* (2013.01)

(56) References Cited

OTHER PUBLICATIONS

Cristofanilli, M., et al., "Circulating Tumor Cells, Disease Progression, and Survival in Metastatic Breast Cancer", N Engl J Med 2004;351:781-91.

Ferreira, M., et al., "Circulating tumor cell technologies", Molecular Oncology, 10 (2016) 374-394.

Joossee, S., et al., "Biology, detection, and clinical implications of circulating tumor cells", EMBO Molecular Medicine vol. 7 | No. 1 | 2015.

Casavant, B., et al., "Paired diagnostic and pharmacodynamic analysis of rare non-small cell lung cancer cells enabled by the VerIFAST platform" Lab Chip. Jan. 7, 2014; vol. 14(1) pp. 99-105.

Casavant, B., et al., The VerIFAST: an integrated method for cell isolation and extracellular/intracellular staining. Lab Chip. Feb. 7, 2013; vol. 13(3) pp. 391-396.

Myung, J., et al., "Microfluidic devices to enrich and isolate circulating tumor cells" Lab Chip, 2015, 15, 4500-4511.

Shields, C., et al., "Microfluidic cell sorting: a review of the advances in the separation of cells from debulking to rare cell isolation" Lab Chip, 2015, 15, 1230-1249.

* cited by examiner

42

Transfer Device  46

Magnet  50

Slide  48

Input Well  44 a) Input Well | Grips locked | Slide | Magnet b)

c) Transfer Device d) Lock Transfer Grips | Unlock Input Well Grips e) Grips Locked | PMP & Cells | Magnet

DEVICES AND METHODS FOR MAGNETIC ISOLATION AND ANALYSIS OF RARE CELLS

CROSS REFERENCE TO RELATED APPLICATION

This application is a Continuation of U.S. patent application Ser. No. 16/095,505 filed Oct. 22, 2018, which is a 35 U.S.C. § 371 U.S. national entry of International Application PCT/US2017/028746, having an international filing date of Apr. 21, 2017, which claims the benefit of U.S. Provisional Application No. 62/325,629, filed Apr. 21, 2016, the content of each of the aforementioned applications is herein incorporated by reference in their entirety.

FIELD OF THE INVENTION

The present invention relates generally to medical devices. More particularly, the present invention relates to devices and method for magnetic isolation and analysis of rare cells.

BACKGROUND OF THE INVENTION

Nearly 150 years ago Thomas Ashworth reported the first observation of circulating tumor cells (CTCs) in the peripheral blood of a patient with metastatic cancer from an unknown primary. Since this early observation, tremendous strides have been made in our technical ability to isolate and analyze these rare cells. This has led to an improved understanding of basic cancer biology as well as a myriad of efforts aimed at exploring CTCs as cancer biomarkers.

It is now understood that CTCs enter the circulation by either passive shedding or through the dynamic processes of invasion and intravasation. Within the circulation, CTCs are required to evade the host immune system and survive sheer stress in order to extravasate at a distant site. Once at their new location, CTCs must adapt to their new microenviroment where they can lay dormant in a quiescent state or undergo proliferation to develop into metastatic foci.

Realizing that CTCs can originate from either primary or metastatic sites of disease, there are a number of potential applications for CTCs as cancer biomarkers. These applications include early cancer diagnosis, disease staging, monitoring for cancer recurrence, prediction of prognosis, and to aid in the selection of therapy. In the field of urologic oncology, CTCs have been explored as biomarkers of prostate, bladder and kidney cancer.

Numerous devices and methods have been developed to try and isolate CTCs in a reproducible and efficient manner. To date, the majority of work has been performed utilizing the CellSearch test, which is the only FDA approved device. This technology, however, is limited by the associated expense and not being able to be used at point-of-care (POC).

Therefore, it would be advantageous to provide a POC, easy to use device for use in the cancer field.

SUMMARY OF THE INVENTION

The foregoing needs are met, to a great extent, by the present invention, wherein in one aspect a device for isolation of a rare cell population includes a surface tension device configured for isolating the rare cell population having a well for receiving a solution containing the rare cell population. The device includes a removable sieve configured to be disposed within the output well for collecting the rare cell population for transfer to a slide. The device also includes a mechanism of extracting the solution from the output well downstream of the sieve.

In accordance with an aspect of the present invention, the device includes a magnet for isolating the rare cell population. The device includes a paramagnetic particle configured for binding cells within the rare cell population. In accordance with another aspect of the present invention, a device for isolation of a rare cell population includes a direct transfer device configured for isolating the rare cell population having an input well for receiving a solution containing the rare cell population. The device also includes a collecting surface configured for collecting cells from the rare cell population of the input well. The device includes a mechanism for holding the collecting surface relative to the input well. The device also includes a magnetic source for isolating the rare cell population. The device includes a paramagnetic particle configured for binding cells within the rare cell population. A paramagnetic particle can be mixed magnetically within the input well. The magnetic source is configured to apply a magnetic force for collecting the rare cells from the receiving well directly onto the collecting surface. The device includes a collecting device configured to attach to the collecting surface. A collecting device and the input well are configured such that both the collecting device and the input well can attach concurrently to the collecting surface and may be detached independent of one another.

In accordance with still another aspect of the present invention, a method of collecting rare cells includes sequentially attaching a collecting surface to an input well. The method includes mixing a solution of paramagnetic particles magnetically with a magnetic source. The method also includes attaching a collecting device. Additionally, the method includes transferring the magnetic source on a side of the collecting device and removing the input well, in order to transfer the rare cells onto the collecting surface under a magnetic force provided by the magnetic source.

In accordance with yet another aspect of the present invention, the method includes fixing the rare cells on the collecting surface for further processing. The method includes isolating the rare cell population with a magnet. The method includes binding cells within the rare cell population with the paramagnetic particles. The method includes mixing the paramagnetic particle solution magnetically within the input well. The method also includes applying magnetic force for collecting the rare cells from the receiving well directly onto the collecting surface. The method includes attaching a collecting device to the collecting surface. The method includes concurrently attaching a collecting device and the input well to the collecting surface and may be detached independent of one another. Additionally, the method includes isolating the rare cell population using a surface tension device having a well for receiving a solution containing the rare cell population. The method also includes positioning a removable sieve configured to be disposed within the output well for collecting the rare cell population for transfer to a slide.

BRIEF DESCRIPTION OF THE DRAWINGS

The accompanying drawings provide visual representations, which will be used to more fully describe the representative embodiments disclosed herein and can be used by those skilled in the art to better understand them and their

US 12,570,944 B2

Figure 1:
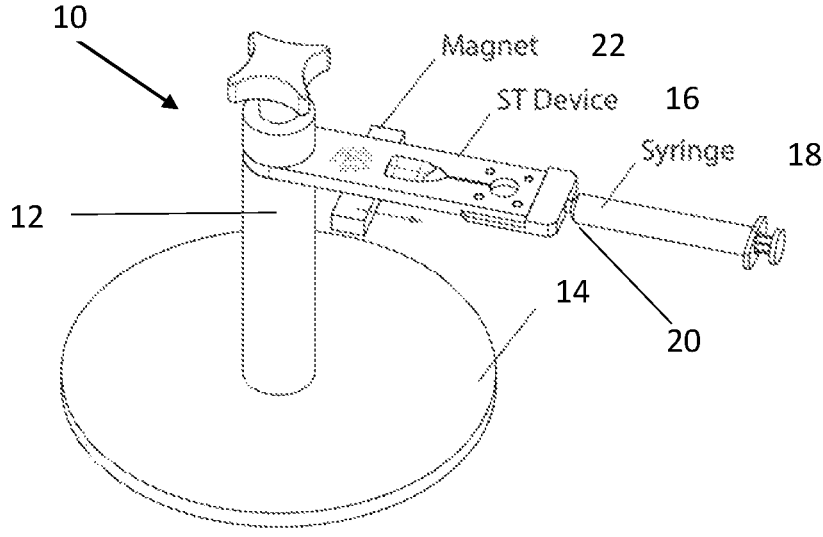

3 inherent advantages. In these drawings, like reference numerals identify corresponding elements and:

FIG. 1 illustrates a perspective view of an overall device for isolation of rare cell populations, according to an embodiment of the present invention.

Figures 2A, 2B, 2C, 2D, 2E:
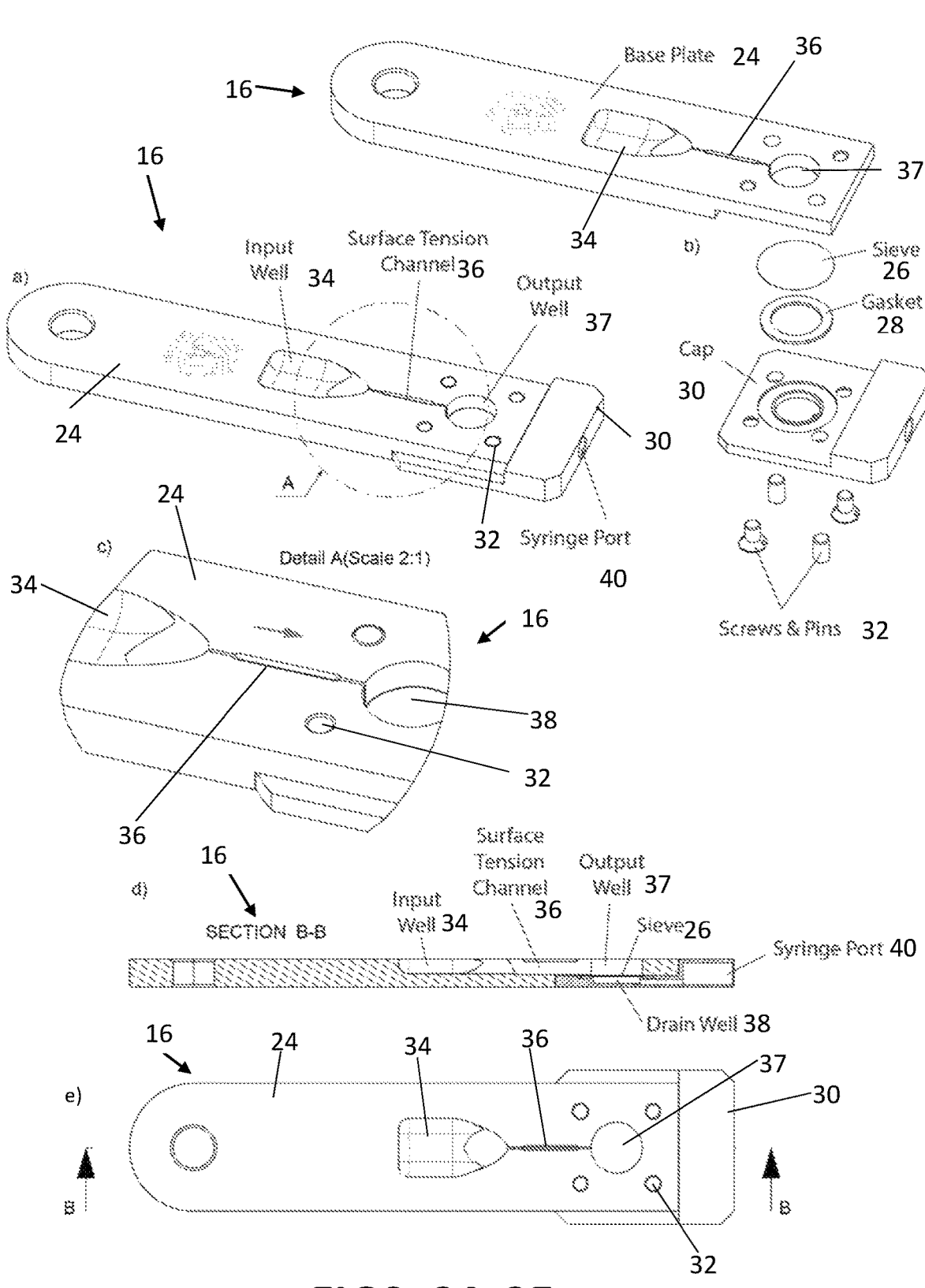

FIGS. 2A-2E illustrate views of the ST device, according to embodiments of the present invention. FIG. 2A illustrates a perspective view of the ST device. FIG. 2B illustrates an exploded view of the ST device. FIG. 2C illustrates a partial view of an end of the ST device. FIG. 2D illustrates a sectional view of the ST device, and FIG. 2E illustrates a top down view of the ST device.

Figure 3:
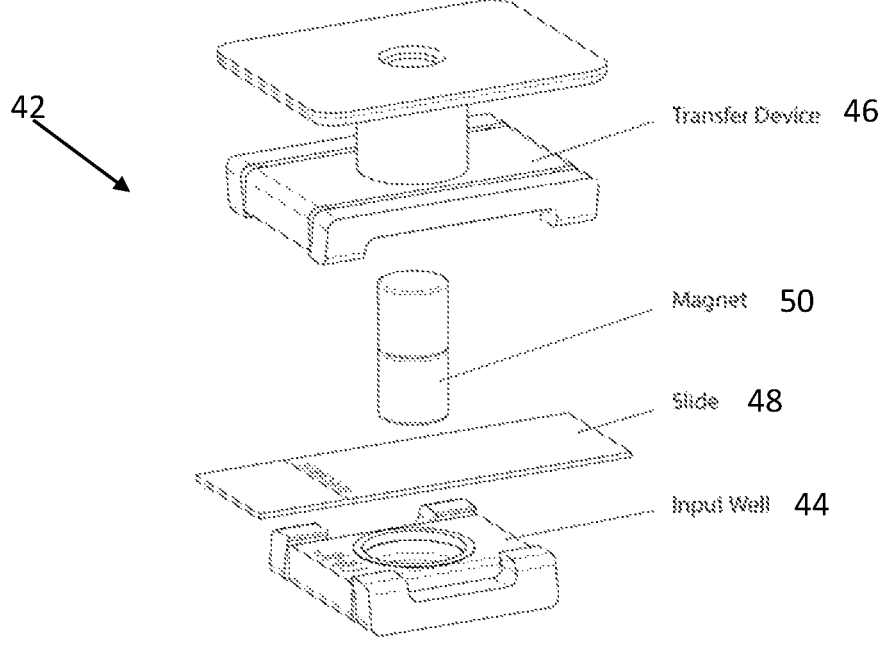

FIG. 3 illustrates an exploded view of a DT device, according to an embodiment of the present invention.

Figures 4A, 4B:
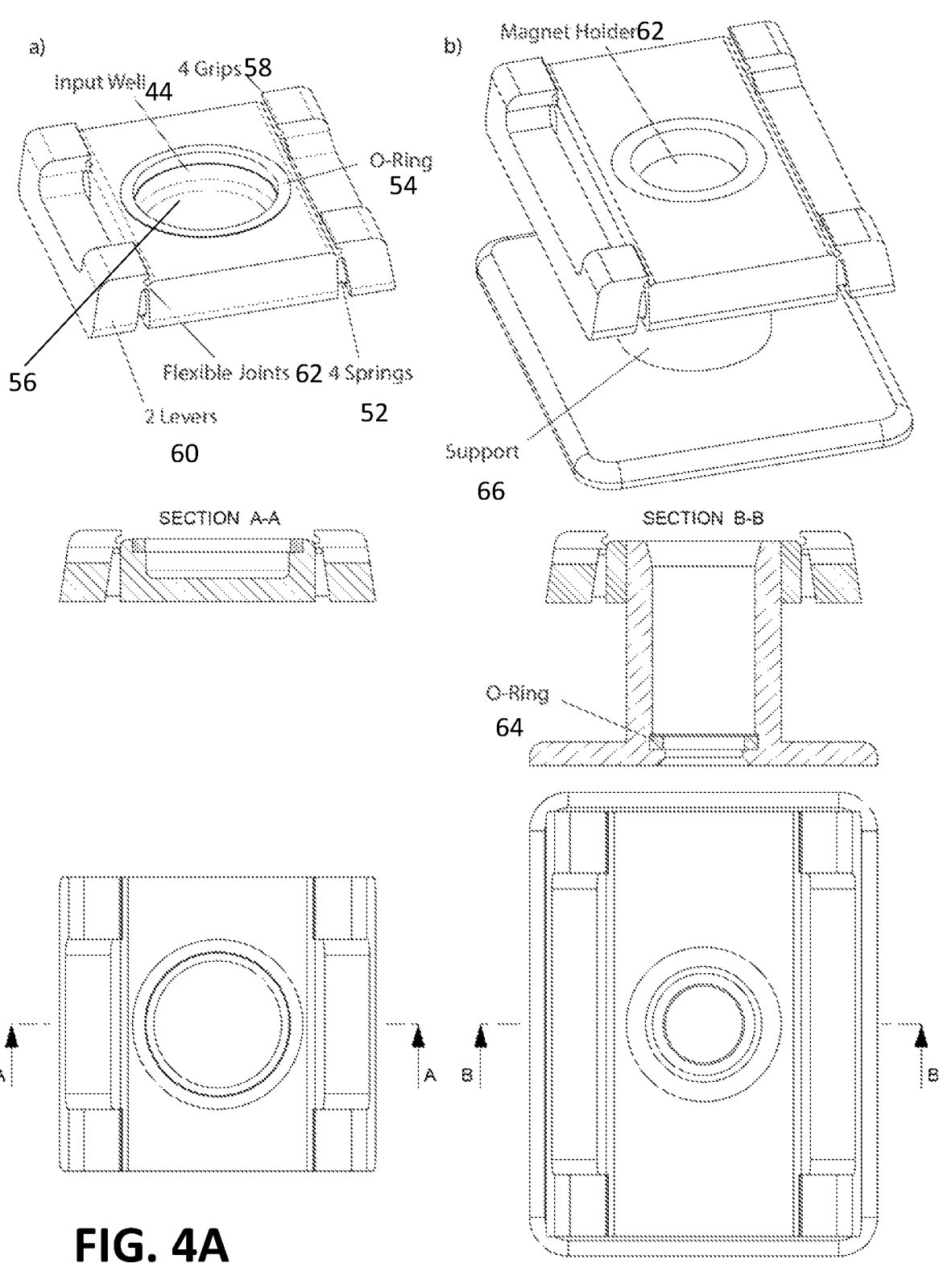

FIGS. 4A and 4B illustrate the input well and transfer device, according to an embodiment of the present invention. FIG. 4A illustrates the input well and FIG. 4B illustrates the transfer device.

Figures 5A, 5B, 5C, 5D, 5E:
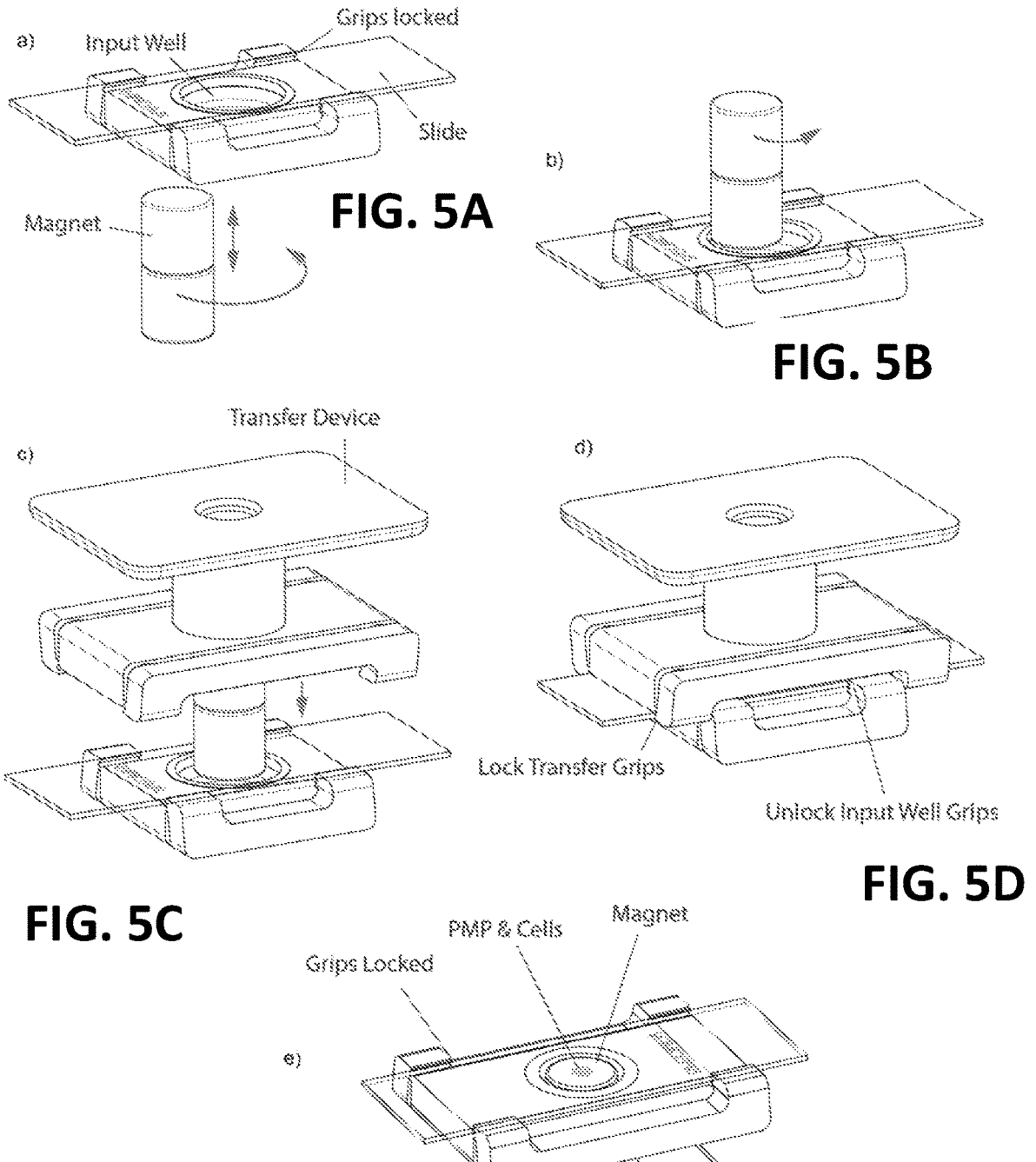

FIGS. 5A-5E illustrate a sequence of steps involved in the operation of the DT device, according to an embodiment of the present invention. FIG. 5A illustrates the input well for receiving the prepared solution. FIG. 5B illustrates the magnet being moved on top of the slide. FIG. 5C illustrates the transfer device being placed over the magnet. FIG. 5D illustrates the transfer device being locked down to the slide. FIG. 5E illustrates the grips being released.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides two devices for the isolation of rare cell populations such as circulating tumor cells (CTCs). Both devices use magnetic fields to manipulate cells that are bounded to paramagnetic particles (PMP). One device uses surface tension and a sieve for cell filtration, whereas the other allows for the direct transfer of cells onto a standard microscope slide. Subsequent processing steps may be directly performed on the devices thereby minimizing cell losses. The first device is referred to as the ST (surface tension) device and the second device is referred to as the DT (direct transfer) device. The ST device can also be considered as a chip for the isolation of the rare cell populations.

FIG. 1 illustrates a perspective view of an overall device for isolation of rare cell populations, according to an embodiment of the present invention. The overall device 10 includes a support 12 with a base 14 that sits on a flat surface, such as a lab bench. The cell isolation portion of the device or ST device 16 mounts in the support 12, so that the cell isolation portion of the device is steadily held in place during operation. A syringe 18 attaches to an end 20 of the ST device 16 configured to receive the syringe 18. A permanent magnet 22 can be movably coupled to the ST device such that the magnet 22 can be manually and freely moved under the ST device 16.

FIGS. 2A-2E illustrate views of the ST device, according to embodiments of the present invention. FIG. 2A illustrates a perspective view of the ST device. FIG. 2B illustrates an exploded view of the ST device. FIG. 2C illustrates a partial view of an end of the ST device. FIG. 2D illustrates a sectional view of the ST device, and FIG. 2E illustrates a top down view of the ST device. The ST device 16 includes a base plate 24, a sieve 26, a sieve gasket 28, and a cap plate 30 that is coupled with dowel pins 32 and attaches to the base plate 24. While dowel pins 32 are described as an exemplary embodiment herein, any suitable way to couple the cap plate 30 to the base plate 24 can also be used. The cap plate 30 mounts and seals the sieve 26 on the base plate 24. The base plate 24 includes an input well 34 with a tapered funnel like surface into a surface tension channel 36. The channel links the input well 34 to an output well 37. The sieve 26 is sealed with the sieve gasket 28 under the output well 37. A drain well 38 located under the surface channel 36 communicates fluid, samples, etc. to a syringe port 40.

In operation, the surface tension channel of the ST device is filled via the input well with a high surface tension solution such as oil. The output well is filled with a washing solution such as a phosphate buffered solution (PBS). A cell suspension derived from a biologic fluid (e.g. blood, urine, bone marrow, saliva, etc.) is admixed with PMPs capable of binding to the rare cells of interest (e.g. via a linking antibody, DNA aptomer, or small molecule). This solution is then placed into the input well and the magnet is placed under this well. The magnetic field produced by the magnet attracts the PMP and thereby also attracts the bound cells.

The magnet is then slowly advanced under the channel towards the output well, therefore displacing the PMP-bound-cells to the output well. The syringe is used to extract the washing solution by passing it through the sieve. The sieve is chosen for a pore size that is capable of trapping the PMP-bound cells of interest. Downstream processing steps such as immunofluorescence or fluorescence in situ hybridization can then be performed directly on the chip. Once these processes are complete, the filter is removed and mounted on a glass slide for microscopic imaging or other analysis.

FIG. 3 illustrates an exploded view of a DT device, according to an embodiment of the present invention. The DT device 42 illustrated in FIG. 3 includes two subassemblies: an input well 44 and a transfer device 46. The DT device 42 can also include a standard microscope slide 48 and a permanent magnet 50. The orientation of the transfer device 46 and the location of the magnet 50 depend on the phase of the operation, as described later.

FIGS. 4A and 4B illustrate the input well and transfer device, according to an embodiment of the present invention. The input well device 44, illustrated in FIG. 4A in a preferred embodiment is constructed in a single part and includes four springs 52 and an O-ring 54. The single piece input well 44 also includes an input well cavity 56 and four grips 58 used to lock down the glass slide on the opening face of the input well cavity 56. The O-ring 54 is also placed at the well opening to seal the input well cavity 56 with the slide. The grips 58 in a preferred embodiment are articulated with flexible joints 62 and are released by depressing the two levers 60 on the sides of the input well device 44. The four springs 52 are used to tension the grips 58. Because the input well device 44 will work with a magnet, all components are made of non-magnetic materials. Preferably, the base is made of plastic, and the O-ring and springs are made of rubber.

As illustrated in FIG. 4B, the transfer device 46 presents a similar construction, so that it can also attach to the slide. However, instead of the input well cavity, the transfer device 46 includes a magnet holder cavity 62. To keep the magnet on the slide, an O-ring 64 is placed at the bottom of the magnet holder cavity 62. In addition, the transfer device 46 includes a support base 66 to stand it on a bench or other flat surface. As shown in FIG. 4B, the body of the transfer device 46 is made of two parts for manufacturing purposes. Depending on the manufacturing process, this could be made in a single or multiple (3) parts, as is known to one of skill in the art.

FIGS. 5A-5E illustrate a sequence of steps involved in the operation of the DT device, according to an embodiment of the present invention. A cell suspension derived from a biologic fluid (e.g. blood, urine, bone marrow, saliva, etc.) is admixed with PMPs capable of binding to the rare cells of interest (e.g. via a linking antibody, DNA strand or small molecule). The prepared cell solution is placed in the input well and the well is sealed with the slide by locking the slide onto the device, as shown in FIG. 5A. The magnets are then moved on a circular path closer and further away from the well. At this step the magnetic field lines crossing the solution engage the PMP, displacing them through the solution in order to increase the likelihood of the PMP to meet the targeted cells and adhere to the PMP. The magnet is then moved on top of the slide and moved on a circular path, as illustrated in FIG. 5B as to gather the PMP and adhered cells from the entire well and attract them on the surface of the slide. With the magnet at the center, the transfer device is placed over the magnet, as illustrated in FIG. 5C and locked down to the slide, as illustrated in FIG. 5D. The grips of the well device are then released, so that the transfer device now holding the slide may be lifted off and placed on a bench on the opposite side, as shown in FIG. 5E. At this point the PMP bound cells of interest are near the center of the slide, held in place by the magnet.

If additional steps (washing, staining, etc.) are desired, these may be performed directly on the slide as usual, but with the added help of the magnet that provides fixation during the process. Imaging of the slide follows in standard manner, after releasing the slide from the transfer device.

The ST chip works in a horizontal rather than vertical orientation making it possible to use a larger capacity input well. Another innovation of the present invention is that the sieve may be removed from the chip for imaging on a standard microscope slide. The DT device and associated method is entirely novel in design and principle of operation. In this case the PMPs and PMP-bound cells are drawn from the input solution and transferred directly on a standard microscope slide. The device eliminates the need for the surface tension channel and washing well. The direct transfer is a substantial advantage because it places the cells directly on the glass slide, reducing the possible loss of cells. If further processing is desired, the DP device provides further magnetic support of the PMP bound cells of interest thus preventing their loss.

The present invention offers advantages over prior devices for cell isolation and analysis. The device of the present invention presents a novel construction with a horizontal rather than a vertical orientation making it possible to use larger capacity wells. Moreover, the integration of the drain well and syringe facilitates downstream processing on the device of the present invention. Most importantly, the sieve may be removed from the device for imaging on a standard microscope slide.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A device for isolation of a rare cell population comprising:
   a direct transfer device configured for isolating the rare cell population having, an input well for receiving a solution containing the rare cell population;
   a collecting surface configured for collecting the rare cell population from the solution received in the input well, wherein the collecting surface takes the form of a microscope slide having a first face and a second face opposite the first face, and wherein a first face of the collecting surface is releasably couplable to the input well; and,
   a magnetic source holder cavity, wherein the magnetic source holder cavity is configured to keep a magnetic source in contact with the second face of the collecting surface to affect transfer of the rare cell population from the solution containing the rare cell population to the collecting surface.

2. The device of claim 1 further comprising springs and an o-ring to lock the collecting surface to the input well.

3. The device of claim 1 further comprising a paramagnetic particle configured to be added to the solution containing the rare cell population for binding cells within the rare cell population.

4. The device of claim 3 wherein the paramagnetic particle is mixed magnetically within the input well.

5. The device of claim 1 further comprising the magnetic source being configured to apply a magnetic force for collecting the rare cells from the input well directly onto the microscope slide.

* * * * *